US008835511B2

(12) United States Patent
Carlucci et al.

(10) Patent No.: US 8,835,511 B2
(45) Date of Patent: *Sep. 16, 2014

(54) ABSORBENT ARTICLES INCLUDING AN ODOR CONTROL SYSTEM

(75) Inventors: Giovanni Carlucci, Chioti (IT); Antonella Pesce, Pescara (IT); Mariangela Caputi, Molfetta (IT); Giancarlo Sierri, Montefino (IT); Alessandro Gagliardini, Villa Vomano (IT)

(73) Assignee: The Procter & Gamble Company, Cincinnati, OH (US)

( * ) Notice: Subject to any disclaimer, the term of this patent is extended or adjusted under 35 U.S.C. 154(b) by 372 days.

This patent is subject to a terminal disclaimer.

(21) Appl. No.: 11/732,580

(22) Filed: Apr. 4, 2007

(65) Prior Publication Data

US 2008/0249490 A1 Oct. 9, 2008

(51) Int. Cl.
*A61K 8/37* (2006.01)
*A61K 8/33* (2006.01)
*A61F 13/84* (2006.01)

(52) U.S. Cl.
CPC .................................. *A61F 13/8405* (2013.01)
USPC ............. 514/701; 514/785; 604/359; 512/26; 512/27

(58) Field of Classification Search
CPC ...................... C11B 9/0019; A61F 2013/8408; A61K 8/37
See application file for complete search history.

(56) References Cited

U.S. PATENT DOCUMENTS

| | | | | |
|---|---|---|---|---|
| 3,607,777 A | * | 9/1971 | Winyall et al. | 423/338 |
| 5,733,272 A | * | 3/1998 | Brunner et al. | 604/359 |
| 5,951,534 A | * | 9/1999 | Cummings et al. | 604/359 |
| 6,048,206 A | | 4/2000 | Johansson | |
| 6,225,524 B1 | * | 5/2001 | Guarracino et al. | 604/359 |
| 6,261,540 B1 | * | 7/2001 | Nelson | 424/53 |
| 6,376,741 B1 | | 4/2002 | Guarracino et al. | |
| 6,503,962 B1 | * | 1/2003 | Mouri et al. | 523/102 |
| 6,753,305 B2 | * | 6/2004 | Raso et al. | 510/438 |
| 6,833,487 B2 | | 12/2004 | Pesce et al. | |
| 6,844,430 B2 | * | 1/2005 | Pesce et al. | 536/20 |
| 6,972,010 B2 | | 12/2005 | Pesce et al. | |
| 7,132,479 B2 | | 11/2006 | Engelhardt et al. | |
| 7,157,411 B2 | | 1/2007 | Rohde et al. | |
| 7,378,453 B2 | | 5/2008 | Nogi et al. | |
| 7,687,452 B2 | | 3/2010 | Kraft | |
| 7,745,685 B2 | | 6/2010 | Fell et al. | |
| 8,034,740 B2 | | 10/2011 | Kitahata et al. | |
| 2001/0023338 A1 | | 9/2001 | Guarracino et al. | |
| 2001/0047157 A1 | * | 11/2001 | Burnett et al. | 604/289 |
| 2003/0022573 A1 | * | 1/2003 | Cintio et al. | 442/96 |
| 2003/0086974 A1 | | 5/2003 | Besemer et al. | |
| 2003/0135172 A1 | | 7/2003 | Whitmore et al. | |
| 2004/0037792 A1 | | 2/2004 | Hiramoto et al. | |
| 2004/0082654 A1 | | 4/2004 | Pesce et al. | |
| 2004/0241333 A1 | * | 12/2004 | Cielenski et al. | 427/421.1 |
| 2005/0131363 A1 | | 6/2005 | MacDonald et al. | |
| 2005/0203473 A1 | | 9/2005 | Pesce et al. | |
| 2007/0065394 A1 | | 3/2007 | Pinney | |

FOREIGN PATENT DOCUMENTS

| | | |
|---|---|---|
| EP | 0 510 619 A1 | 10/1992 |
| EP | 0 811 387 B1 | 3/2003 |
| JP | 08 127506 | 5/1996 |
| JP | 08127506 | 5/1996 |
| JP | 3127549 | 1/2001 |
| JP | 4446650 | 4/2010 |
| WO | WO 97/46187 A1 | 12/1997 |
| WO | WO 97/46189 A1 | 12/1997 |
| WO | WO 97/46192 A1 | 12/1997 |
| WO | WO 98/26808 A2 | 6/1998 |
| WO | WO03/076700 | 9/2003 |

OTHER PUBLICATIONS

PCT International Search Report dated Feb. 13, 2008.
Evaluation Techniques, 4th Ed., by Meilgaard, Civille, and Carr, © 2007 by Taylor & Francis Group, LLC/CRC Press, pp. 47, 56-60, 93.
PCT International Search Report dated Jul. 9, 2007.

\* cited by examiner

*Primary Examiner* — Sue Liu
*Assistant Examiner* — Jessica Kassa
(74) *Attorney, Agent, or Firm* — Andrés E. Velarde; Megan C. Hymore; Brian M. Bolam

(57) ABSTRACT

Absorbent articles provided with an odor control system. The odor control system includes at least two classes of odor control materials, wherein one class acts on malodors or a malodorous substance in the absorbent article and a second class acts on nose receptors. The classes of odor control materials may be selected to provide a synergistic effect in terms of malodor reduction.

11 Claims, No Drawings

ABSORBENT ARTICLES INCLUDING AN ODOR CONTROL SYSTEM

FIELD OF THE INVENTION

The present invention relates to absorbent articles which are provided with an odor control system. The odor control system comprises classes of odor control materials, wherein one class reduces malodors by acting on the malodors or malodorous substance and a second class acts on nose receptors. The classes of odor control materials may be selected to provide a synergistic effect in terms of malodor reduction.

BACKGROUND OF THE INVENTION

Absorbent articles of personal hygiene are known in the art. Typical examples include sanitary napkins, panty liners, adult incontinence articles, infant diapers, paper towels, bath tissue and facial tissue. Such articles are often used to absorb and retain bodily fluids and other exudates excreted by the human body. Typically, such exudates are perceived as malodorous and offensive. Therefore, methods and materials for controlling and reducing malodors in absorbent articles have been developed. Some examples are discussed hereinafter.

An early, basic reference in this respect is EP 510 619. This document discloses a wide variety of materials, which have proven to be effective in certain circumstances in reducing malodors in absorbent articles of personal hygiene. EP 959 846 discloses such materials comprising polyacrylate superabsorbers and silica. EP 811 387 discloses absorbent articles being provided with a zeolite and silica odor control system. EP 963 186 discloses an odor control systems comprising zeolites, silica and polyacrylic superabsorbers. EP 912 149 discloses chelating agents for use in odor control in absorbent articles, particularly polyfunctionally substituted aromatic chelants.

Although, the above solutions may provide a consumer-noticeable degree of malodor reduction in absorbent articles, due to the nature of action and the materials chosen, only a limited variety of malodorous compounds can be counteracted.

Therefore it is desirable to provide absorbent articles having an odor control system, which acts against a wide variety of malodors in a holistic manner. It is also desirable to provide an absorbent article having an odor control system including at least one class of materials that reduces malodors by acting on malodors or a malodorous substance in the article and/or at least one class that acts on certain nose receptors. It would also be desirable to provide an absorbent article including an odor control system having at least one material that acts on the malodors and/or malodorous substance to reduce the odor and the same or another material that acts on nose receptors to help reduce the perception of malodor.

SUMMARY OF THE INVENTION

The present invention addresses the above need by providing an absorbent article having an odor control system. The odor control system includes at least two classes of odor control materials. The first class of odor control material reduces odor by acting on malodors or a malodorous substance in the absorbent article. The second class of odor control material reduces odor by acting on the user's nose receptors. The first class of odor control material is selected from the group consisting of silica gel having a pH of less than 7, aldehydes, mesoporous zeolites having pores sizes of from 20 to 500 Å and mixtures thereof, wherein said aldehydes are selected from the group consisting of α-amylcinnamic aldehyde, p-anisaldheyde, benzaldehyde, cinnamic aldehyde, cuminic aldehyde, decanal, p-t-butyl-alpha-methyldihydrocinnamaldhyde, 4-hydroxy-3-methoxycinnamaldehyde, 2-phenyl-3-(2-furyl)prop-2-enal, vanillin isobutyrate, ethyl vanillin acetate, vanillin acetate, cyclamen aldehyde, heptanal, lauryl aldehyde, nonanal, octanal, phenylacetaldehyde, phenyl propyl aldehyde, vanillin, salycil aldehyde, cytral and mixtures thereof. The second class of odor control material is selected from the group consisting of menthol, menthyl acetate, 3-buten-2-one,3-methyl-4-(2,6,6-trimethyl-2-cyclohexen-1-yl), 4-(2,6,6-trimethylcyclohen-1-en-1-yl)but-3-en-2-one, 3-buten-2-one,4-(2,6,6-trimethyl-2-cyclohexen-1-yl), menthyl lactate, isomenthyl acetate, isomenthyl propionate, isomenthyl isobutyrate, isomenthyl propionate, isomenthyl butyrate, camphor, p-menthane and mixtures thereof.

DETAILED DESCRIPTION OF THE INVENTION

The term "absorbent article" is used herein in a very broad sense including any article able to receive and/or absorb and/or contain and/or retain fluids and/or exudates, especially bodily fluids/bodily exudates. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and preferably to be recycled, composted or otherwise disposed of in an environmentally compatible manner). Typical disposable absorbent articles according to the present invention are diapers, surgical and wound dressings and perspiration pads, incontinence pads, as well as absorbent articles for feminine hygiene like sanitary napkins, panty liners, tampons, interlabial devices or the like. Certain absorbent articles include a fluid pervious topsheet, a fluid impervious backsheet that is preferably water vapor and/or gas pervious and an absorbent core comprised there between.

The term "use", as used herein, refers to the period of time that starts when the absorbent article is actually put in contact with the anatomy of a wearer. It is further underlined that the odor neutralization benefits provided by the absorbent articles of the present invention are already provided as soon as the absorbent articles is released from its package. This is due to the volatility of the odor neutralization materials acting on nose receptors (sometimes referred to herein as acting "externally"), which are further specified below.

By "body fluid" it is meant herein any fluid produced by human body including, but not limited to, perspiration, urine, menstrual fluids, vaginal secretions and the like.

The present invention also relates to an odor control system, which reduces the malodor generated by a broad range of odorous materials typically occurring in or resulting from the degradation of body fluids and/or materials making up the absorbent article. The odor control system includes at least two classes of odor control materials; one class of odor control materials counteracts the malodors of the exudates or other malodorous material (also referred to herein as acting "internally"), whereas a second class counteracts such malodors by affecting the receptors in the nose.

Odor Control Materials Acting on the Malodors or Malodorous Substance

There are many materials known in the art for counteracting malodors in absorbent articles. Examples can be found in the references cited herein before. Typical substances are zeolites, starch, activated carbon, cyclodextrine, chitin or chitosan and esters.

These actives can reduce the malodor unpleasantness according to different mechanisms, e.g. they can reduce the amount of malodorous molecules through absorption/adsorption mechanisms and/or can react with the malodorous molecules transforming them into low volatile/non-odorous ones and/or can suppress malodorous molecules volatility and/or can prevent the malodor generation by inhibiting degradative processes caused by micro-organisms metabolic activity.

For the odor control system of the present invention, a specific selection of such materials is desired. It has been found that silica gel, aldehydes and mesoporous zeolites are particularly useful.

Silica gel is a porous, amorphous form of silica ($SiO_2$). It is composed of a vast network of interconnected microscopic pores. As opposed to zeolites, silica gels have larger pores with a wide range of diameters typically between 5 Å and 3000 Å.

Silica gel, which has proven particularly useful in the odor control system herein is the narrow silica gel with a pH of less than 7. Indeed, it was discovered that this type of silica gel is effective in reducing the malodor level according to two different types of odor control mechanisms: absorption/adsorption of malodorous molecules on silica surface and neutralization of aminic components. The latter are a main source of malodor especially in feminine hygienic products. Silica gels with a pH of less than 6 may be desirable for certain embodiments.

It is possible to adjust the silica gel pore size range in the manufacturing process: Silica gels synthesized with an average pore size of about 10-50 Å are known as "narrow" pore silica gels; silica gels with an average pore size of about 110 Å and beyond are called "wide" pore silica gels. Silica gels with wide pore are generally more expensive than narrow silica gel. In certain embodiments, the silica gel used is the narrow silica gel with average pore size of from 20-40 Å, or in some embodiments 30 Å.

One suitable silica gel herein has a total surface area higher than 500 m$^2$/g. The total surface area can be established by using the BET (Brunauer-Emmett-Teller) test. This test is based on the adsorption of nitrogen gas at 77 K onto the surfaces of the silica gel particles, i.e. also their internal cavities. The adsorbed volume of nitrogen is then established by comparing the nitrogen pressure before and after the adsorption. Exemplary suitable silica gel materials include silica gel code 122 and 123 available from Grace, Columbia, Md., USA.

It has further been found that narrow silica gel or zeolites, especially mesoporous zeolites, can be used to stabilize the volatile odor control materials acting externally in the absorbent article. Mesoporous zeolites are those zeolites with pore size from 20 to 500 Å. As indicated above, silica gel can absorb volatile substances and thus reduces its migration out of the absorbent article. Advantageously, this may prolong the shelf life of absorbent articles.

Without being bound by theory, it is assumed that narrow silica gel can adsorb the most volatile and active compounds due to its porosity, particularly by creation of hydrogen bonding, and easily release active compounds during usage of product, i.e. due to presence of water that competes with the absorbed molecules in the formation of hydrogen bonds with the silica gel surface.

The stabilization effect has been proven by running a Thermogravimetric analysis (TGA) on samples of narrow silica gel treated with 10 weight-% of menthyl acetate. Specifically, the method is based on evaluation of weight loss over time at specific temperature (40° C.). The samples were kept at 40° C. for 180 minutes. In order to have a basis for comparison the TGA analysis was performed on a sample of pure menthyl acetate and a sample of pure silica gel as references together with a sample of menthyl acetate (10%)+silica gel (ex Grace, coded 123). The results are listed in table 1 and illustrate that the sample with silica gel and MA has a significant lower weight loss than the samples of menthyl acetate alone.

TABLE 1

| Data point | Sample composition | Weight Loss (%) |
|---|---|---|
| 1 | Menthyl acetate | ~100% |
| 2 | Silica gel + Menthyl acetate | 3 |
| 3 | Silica gel | 3 |

One component of body fluid malodor is ammonia. For example ammonia is present in high amounts in products used for urine absorption due to degradation of urea. Ammonia and its derivatives can react with aldehyde to form imines (according to the so-called Schiff base reaction).

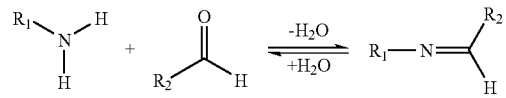

This reaction is catalyzed by enzymes and/or by a slightly acidic pH 4 to 5. The moderate acid requirement is necessary to allow protonation of the hydroxyl intermediate to allow water to leave.

Unfortunately, most aldehydes capable of imine reaction have an unpleasant and/or an intense odor that can be disturbing to the human nose and/or they are very volatile and are not stable on the product. Therefore, it is desirable to select suitable materials for controlling malodor. Examples of suitable aldehydes for controlling malodor are those aldehydes that are able to react with aminic compounds according to Schiff base reaction and have not unpleasant odor. Suitable aldheydes include α-amylcinnamic aldehyde, p-anisaldheyde, benzaldehyde, cinnamic aldehyde, cuminic aldehyde, decanal, p-t-butyl-alpha-methyldihydrocinnamaldehyde, 4-hydroxy-3-methoxycinnamaldehyde, 2-phenyl-3-(2-furyl)prop-2-enal, vanillin isobutyrate, ethyl vanillin acetate, vanillin acetate, cyclamen aldehyde, heptanal, lauryl aldehyde, nonanal, octanal, phenylacetaldehyde, phenyl propyl aldehyde, vanillin, salycil aldehyde, cytral and mixtures thereof. Some of the most desirable aldehydes for application herein are alpha-amylcinnamaldehyde and decanal.

Odor Control Materials Acting on Nose Receptors

The second class of odor control materials in the odor control systems counteracts odors externally, outside the absorbent articles. Specifically, the materials listed hereinafter inhibit the receptors of the nose, hereinafter called "nose blocking". When used, these materials may significantly reduce the capability for the nose to detect the malodors.

The nose blocking is possible due to the volatile nature of the materials selected, which are evaporating out of the absorbent article and are then inhaled into the nose of an individual generally within somewhat close range of the article, e.g. within about 0 to about 10 meters of the article (although this should in no way be intended to limit the scope of the invention) by normal breathing. The blocking of the nose receptors is of course only temporary.

Suitable nose blocking materials include menthol, menthyl acetate, 3-buten-2-one,3-methyl-4-(2,6,6-trimethyl-2-cyclohexen-1-yl), 4-(2,6,6-trimethylcyclohen-1-en-1-yl)but-3-en- 2-one, 3-buten-2-one,4-(2,6,6-trimethyl-2-cyclohexen-1-yl), menthyl lactate, isomenthyl acetate, isomenthyl propionate, isomenthyl isobutyrate, isomenthyl propionate,isomenthyl butyrate, camphor and p-menthane. The materials also include their isomeric forms, diastereomers and enantiomers. Advantageously, in general, the above materials have only a very slight inherent odor but show a high degree of nose receptor blocking.

Optional Further Components
a) High Vapor Pressure Materials

The action of the odor control system of the present invention can be further improved by providing the absorbent article with a highly volatile component. According to the law of Dalton, due to their high partial pressure in the headspace of the absorbent article, such highly volatile components are believed to reduce the molar fraction of the malodorous compounds having a lower partial pressure.

Suitable highly volatile components include materials that have a KI (Kovat Index) below 1500 and pleasant odor. The Kovat Index is defined by the selective retention of perfume raw materials (PRMs) onto chromatographic columns (30M× 0.25 mm DB51u 50-300 @4 12.0 psi; Constant Flow, available from Agilent Technologies Inc (ex J&W Scientific)). A PRM's polarity, molecular weight, vapor pressure, boiling point, and the stationary phase property determine the extent of retention.

"Suitable highly volatile components that act according to this mechanism include, for example, limonene, eucalyptol, cresol, linalool, tetra-hydrolinalool, myrcenol, tetra hydromyrcenol, dihydromyrcenol, myrcene, cytronellol, cytronellyil derivatives, geraniol, geranyl derivatives, linalyl acetate, mugetanol, eugenol, jasmal, terpineol, pinanol, cedrene, damascone, beta pinene, cineole and its derivatives, nonadienol, ethylhexanal, octanol acetate, methyl furfural, terpinene, thujene, amylacetate, benzylacetate, camphene, citronellal, dihydrocumarin, dihydromyrcenyl acetate, geraniol, geranial, isoamylacetate, ethyl, and/or triethyl acetate, para-cresol and para-cymene."

b) Solvents

Further additional ingredients include solvents as carriers for incorporating the odor control materials into the absorbent article. Suitable exemplary solvents are e.g. benzyl-benzoate, isopropyl myristate, methyl abietate, ethanol, isopropanol, diethylene glycol monoethyl ether, glycerol, propylene glycol, 1,2-butylene glycol, dipropylene glycol, 2-methyl-2,4-pentanediol, diethyl phthalate, trietyl citrate, diethyl sebacate.

The Odor Control System

It has been found that the combination of certain, separately known odor control materials results in a synergistic effect in terms of odor reduction. Specifically, a synergistic effect in terms of malodor reduction is observed when combining odor control materials acting on the malodors or malodorous substance itself and odor control materials acting on nose receptors, as described above. In fact, an odor control system combining actives of the aforementioned two classes may reduce the malodors more efficiently than the mathematical combination of each material acting individually.

Without wishing to be bound by theory this is believed to be a result of the neutralization of the malodorous molecules in the absorbent article by the odor control materials acting internally, which reduces the concentration of these molecules in the head space and thus, in the air. Due to this, the odor control material acting externally onto the nose receptors can exploit their maximum activity.

When the odor control system of the present invention is used in absorbent articles the individual odor control materials can be employed at variable amounts. Starting with the odor control material acting internally, for silica gel an amount of from about 5 g/m$^2$ to about 300 g/m$^2$, or from about 20 g/m$^2$ to about 100 g/m$^2$ has proven useful. For cinnamic aldehyde, an amount of from about 0.05 g/m$^2$ to about 20 g/m$^2$, or from about 0.5 g/m$^2$ to about 0.5 g/m has proven useful. An example of an odor control material acting on nose receptors includes menthyl acetate in the range from about 0.05 g/m$^2$ to about 20 g/m$^2$, or from about 0.5 g/m$^2$ to about 5 g/m$^2$.

The odor control system comprises the first class of odor control material, acting on the malodors or malodorous substance, in relation to the second class of odor control material, acting on the nose receptors, at a ratio of from about 50:1 to about 1:50 by weight, or from about 30:1 to about 1:30 by weight or from about 1:15 to about 15:1 by weight. In one embodiment, the odor control system comprises silica gel and menthyl acetate at a ratio of about 15:1 by weight. In an alternative embodiment the odor control system comprises alpha-amylcinnamaldehyde and menthyl acetate at a ratio of about 1:1 by weight.

Absorbent Article

The absorbent article being provided with the odor control system herein can be any kind of absorbent article of personal hygiene known in the art. The odor control system of the present invention can be present in any part of the absorbent article. According to the present invention the odor control system can be either be present in the absorbent article as an intimate mixture of the at least two classes of odor control materials or with both classes of odor control materials being separate from each other.

In one embodiment of the present invention, the odor control system is present in the absorbent core. In another embodiment of the present invention, the odor control system is present in or on a secondary topsheet which might be present between the topsheet, which is the uppermost layer of the absorbent article, and the absorbent core. A further embodiment of the present invention has the first class of odor control materials (acting on the malodors or malodorous substance) placed on the wearer-facing surface of the absorbent core and the second class of odor control materials (acting on nose receptors) placed on the garment-facing surface of the absorbent core. Taking into account the stabilization described herein before, one execution of this embodiment is an absorbent article being provided with silica gel on the wearer-facing surface of the absorbent core and with menthyl acetate of the garment-facing surface of the absorbent core. However, other arrangements of the first and second odor control materials are contemplated, including placing them in other elements of the article and/or providing one or more of them separate from the article.

Test Methods and Data

For proving the synergistic effect on odor reduction several test samples are prepared by exposing them to a 0.1% aqueous solution of ammonia, which serves as a test malodorous substance. The first data point in table 2 serves as a benchmark as it represents the degree of unpleasantness of the ammonia solution without added odor control material. Data points 2-3 in table 2 are illustrating the malodor-reducing activity of two exemplary odor control materials alone, specifically alpha-amylcinnamaldehyde as exemplary aldehyde and menthyl acetate as an exemplary odor control material acting on the nose receptors.

The last data point 4 in table 2 is illustrating the activity of the odor control system of the present invention. For comparability, two individual odor control materials were mixed at half their amount compared to data points 2-3. Data point 4 was obtained by testing a mixture of alpha-Amylcinnamaldehyde and menthyl acetate. It is clear from data point 4 that the odor reduction performance of the odor control system is significantly better than that of the individual odor control materials. Thus, synergistic odor control activity has been proven.

TABLE 2

| Data point # | Sample composition | Odor unpleasantness (%) |
|---|---|---|
| 1 | Malodorant solution (10 ml) | 100 |
| 2 | Alpha-Amylcinnamaldehyde (16 mg) + Malodorant solution (10 ml) | 64 |
| 3 | Menthyl acetate (16 mg) + Malodorant solution (10 ml) | 46 |
| 4 | Alpha-Amylcinnamaldehyde (8 mg) + Menthyl acetate (8 mg) + Malodorant solution (10 ml) | 30 |

Further, odor unpleasantness and pleasantness of these samples was evaluated by a panel of expert graders. In particular, five different expert graders evaluated 4 replicates for each sample. Odor unpleasantness was evaluated by using a scale from −10 to +0, where—10 indicates the max odor unpleasantness, 0 indicates no odor. Data was then reported as % relative unpleasantness vs. Reference (malodorant solution). The odor evaluation was performed in adequate room, at controlled T (25° C.). The room was equipped with appropriate conditioning system allowing continuous exchange of air. The samples were held in numbered metal trays, which were covered with aluminum foil between the actual gradings.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Each dimension for which a value is defined herein is a technical dimension, which, in the context of the present invention is not to be understood literal. Hence, all embodiments having dimensions functionally equivalent to the dimensions stated herein are intended to be covered by the scope of the invention, e.g. a dimension of "40 mm" has to be understood as meaning "about 40 mm".

What is claimed is:

1. An absorbent article comprising an odor control system, the odor control system comprising two classes of odor control material:
   a first class of volatile odor control material that reduces odor by acting on malodors or a malodorous substance in the absorbent article, the first class of odor control material consisting of alpha-amylcinnamaldehyde in an amount of from about 0.05 $g/m^2$ to about 20 $g/m^2$; and
   a second class of volatile odor control material that reduces odor by inhibiting the user's nose receptors, the second class of odor control material consisting of menthyl acetate; and
   wherein the odor control system comprises the alpha-amylcinnamaldehyde and menthyl acetate at a ratio of about 1:1 by weight.

2. An absorbent article comprising an odor control system, the odor control system comprising two classes of odor control material and a solvent:
   a first class of volatile odor control material that reduces odor by acting on malodors or a malodorous substance in the absorbent article, the first class of odor control material consisting of α-amylcinnamic aldehyde in an amount of from about 0.05 $g/m^2$ to about 20 $g/m^2$;
   a second class of volatile odor control material that reduces odor by inhibiting the user's nose receptors, the second class of odor control material consisting of menthyl acetate; and
   a solvent for incorporating the two classes of odor control material into the absorbent article, the solvent selected from the group consisting of benzyl-benzoate, isopropyl myristate, methyl abietate, ethanol, isopropanol, diethylene glycol monoethyl ether, glycerol, propylene glycol, 1,2-butylene glycol, dipropylene glycol, 2-methyl-2,4-pentanediol, diethyl phthalate, trietyl citrate, diethyl sebacate, and combinations thereof;
   wherein the odor control system comprises the alpha-amylcinnamaldehyde and menthyl acetate at a ratio of about 1:1 by weight; and
   wherein the odor control system provides a synergistic effect in malodor reduction compared to the first class of odor control materials or the second class of odor control materials alone, and wherein the odor control system provides neutralization benefits as soon as the absorbent article is released from a package.

3. The absorbent article of claim 2, wherein the odor control system further comprises a highly volatile component selected from the group consisting of limonene, eucalyptol, cresol, linalool, tetra-hydrolinalool, myrcenol, tetra hydromyrcenol, di-hydromyrcenol, myrcene, cytronellol, cytronellyil derivatives, geraniol, geranyl derivatives, linalyl acetate, mugetanol, eugenol, jasmal, terpineol, pinanol, cedrene, damascone, beta pinene, cineole and its derivatives, nonadienol, ethylhexanal, octanol acetate, methyl furfural, terpinene, thujene, amylacetate, benzylacetate, camphene, citronellal, dihydrocumarin, dyhydromyrcenyl acetate, geraniol, geranial, isoamylacetate, ethyl, and/or triethyl acetate, para-cresol, para-cymene, and mixtures thereof.

4. The absorbent article of claim 2, wherein the odor control system comprises alpha-amylcinnamaldehyde in an amount of from about 0.5 $g/m^2$ to about 5 $g/m^2$.

5. The absorbent article of claim 2, wherein the odor control system comprises menthyl acetate in an amount of from about 0.05 $g/m^2$ to about 20 $g/m^2$.

6. The absorbent article of claim 2, wherein the odor control system comprises menthyl acetate in an amount of from about 0.5 $g/m^2$ to about 5 $g/m^2$.

7. The absorbent article of claim 2, wherein the odor control system is provided as a mixture of the two classes of odor control materials.

8. The absorbent article of claim 2, wherein the first class of odor control material and the second class of odor control materials are provided on the absorbent article separate from each other.

9. The absorbent article of claim 2, wherein the absorbent article comprises a topsheet, a backsheet, and an absorbent core provided between the topsheet and the backsheet, and the odor control system is present in the absorbent core.

10. The absorbent article of claim 2, wherein the absorbent article comprises a topsheet, a backsheet, an absorbent core provided between the topsheet and the backsheet, and a secondary topsheet provided between the topsheet and the absorbent core, and the odor control system is provided on the secondary topsheet.

11. The absorbent article of claim 2, wherein the absorbent article comprises a topsheet, a backsheet, and an absorbent core provided between the topsheet and the backsheet, the absorbent core having a wearer-facing surface and a garment-facing surface, and wherein the first class of odor control materials is placed on the wearer-facing surface of the absorbent core and the second class of odor control materials is placed on the garment-facing surface of the absorbent core.

* * * * *

UNITED STATES PATENT AND TRADEMARK OFFICE
CERTIFICATE OF CORRECTION

| | | |
|---|---|---|
| PATENT NO. | : 8,835,511 B2 | Page 1 of 2 |
| APPLICATION NO. | : 11/732580 | |
| DATED | : September 16, 2014 | |
| INVENTOR(S) | : Giovanni Carlucci et al. | |

It is certified that error appears in the above-identified patent and that said Letters Patent is hereby corrected as shown below:

On the title page

Item 75 in the list of inventors, delete "Chioti" and insert -- Chieti --.

In the claims

Column 7
Lines 60 - 67, delete "1. An absorbent article comprising an odor control system, the odor control system comprising two classes of odor control material:
a first class of volatile odor control material that reduces odor by acting on malodors or a malodorous substance in the absorbent article, the first class of odor control material consisting of alpha-amylcinnamaldehyde in an amount of from about 0.05 $g/m^2$ to about 20 $g/m^2$; and".

Column 8
Lines 1 - 7, delete "a second class of volatile odor control material that reduces odor by inhibiting the user's nose receptors, the second class of odor control material consisting of menthyl acetate; and wherein the odor control system comprises the alpha amylcinnamaldehyde and menthyl acetate at a ratio of about 1:1 by weight.".

Line 8, delete "2" and insert -- 1 --.

Line 37, delete "3" and insert -- 2 -- and delete "2" and insert -- 1 --.

Line 41, delete "di-hydromyrcenol" and insert -- dihydromyrcenol --.

Line 47, delete "dyhydromyrcenyl" and insert -- dihydromyrcenyl --.

Line 50, delete "4" and insert -- 3 -- and delete "2" and insert -- 1 --.

Signed and Sealed this
Sixteenth Day of August, 2016

Michelle K. Lee
*Director of the United States Patent and Trademark Office*

CERTIFICATE OF CORRECTION (continued)
U.S. Pat. No. 8,835,511 B2

Line 53, delete "5" and insert -- 4 -- and delete "2" and insert -- 1 --.

Line 56, delete "6" and insert -- 5 -- and delete "2" and insert -- 1 --.

Line 59, delete "7" and insert -- 6 -- and delete "2" and insert -- 1 --.

Line 62, delete "8" and insert -- 7 -- and delete "2" and insert -- 1 --.

Line 66, delete "9" and insert -- 8 -- and delete "2" and insert -- 1 --.

<u>Column 9</u>
Line 3, delete "10" and insert -- 9 -- and delete "2" and insert -- 1 --.

Line 9, delete "11" and insert -- 10 -- and delete "2" and insert -- 1 --.

Line 19, insert -- 11. An absorbent article comprising an odor control system, the odor control system comprising two classes of odor control material:
    a first class of volatile odor control material that reduces odor by acting on malodors or a malodorous substance in the absorbent article, the first class of odor control material consisting of alpha-amylcinnamaldehyde in an amount of from about 0.05 $g/m^2$ to about 20 $g/m^2$; and
    a second class of volatile odor control material that reduces odor by inhibiting the user's nose receptors, the second class of odor control material consisting of menthyl acetate; and
wherein the odor control system comprises the alpha-amylcinnamaldehyde and menthyl acetate at a ratio of about 1:1 by weight. --.